United States Patent [19]

Misch et al.

[11] Patent Number: 4,941,631
[45] Date of Patent: Jul. 17, 1990

[54] SEMI-MICRO MANIPULATOR

[76] Inventors: Donald W. Misch, Department of Biology, Coker Hall 010A, Campus Box 3280, University of North Carolina; Irvine R. Hagadorn, deceased, late of Northwood Dr.; by Thomas D. Higgins, III, legal representative, 820 Airport Rd., all of Chapel Hill, N.C. 27514; William M. Darby, 9701 A Reichsford Rd., Ijamsville, Md. 21754; Murray S. Swanson, 9549 Longs Mill Rd., Rocky Rodge, Md. 21778

[21] Appl. No.: 75,900

[22] Filed: Jul. 10, 1988

[51] Int. Cl.$^5$ .............................. F16M 11/00
[52] U.S. Cl. ................................ 248/178; 248/187; 248/206.5; 403/DIG. 1; 403/61
[58] Field of Search ............... 269/71; 248/178, 206.5, 248/299, 359 A, 179, 187, 467, 476, 544, 558; 52/DIG. 4; 211/DIG. 1; 403/DIG. 1, 61; 33/DIG. 1

[56] References Cited

U.S. PATENT DOCUMENTS

| 2,336,104 | 12/1943 | Laube et al. | 248/178 |
| 2,787,836 | 4/1957 | White | 248/206.5 X |
| 2,876,359 | 3/1959 | Plymale | 248/206.5 |
| 3,881,888 | 5/1975 | Schwab | 269/71 X |
| 3,926,422 | 12/1975 | Wilson | 269/71 X |
| 4,538,354 | 9/1985 | Smolik | 33/DIG. 1 X |
| 4,635,376 | 1/1987 | Fry | 33/DIG. 1 X |
| 4,792,051 | 12/1988 | Miller | 211/DIG. 1 X |

Primary Examiner—David L. Talbott

[57] ABSTRACT

The invention is directed to an apparatus for manipulating and precisely positioning devices, such as microinjectors, in relation to small (less than 100 micron diameters) organisms and objects in order to conduct various research activities thereon. The invention has a high degree of flexibility and stability due to its method of construction to include the use of magnetic force to attach certain of the appratus' components to each other.

8 Claims, 1 Drawing Sheet

SEMI-MICRO MANIPULATOR

BACKGROUND OF THE INVENTION

This invention relates to a manipulating/positioning apparatus and, more specifically, to an apparatus used in medical research for holding and manipulating a micro-injector or other device requiring precise positioning in order to make metered injections or physiological measurements, or conduct other experiments on small organisms and other objects.

Often medical research requires the conduct of experiments in connection with very small living organisms (less than 100 micron diameters) such as mosquito larvae and other delicate objects. For example, such experiments may require researchers to inject substances into an opening in an organism without killing it.

Such injections require an injection device and an apparatus which can be manipulated in all directions in very small increments, and, once in position, will not move due to backlash, oscillation, settling or momentum.

SUMMARY OF THE INVENTION

The problems described above are solved, to a great extent, through the practice of the invention. Illustratively, a base is provided on which is placed a pedestal. The pedestal, which consists of a vertical member sitting perpendicularly on top of a horizontal member, can be slidably moved in relation to the base by turning a threaded rod which is attached to the base and threadably engages the pedestal.

Attached to the vertical member of the pedestal is a pointer which holds the micro-injector or other device used on the organism or object under study. The pointer can be positioned at a variety of angles in relation to the pedestal and base. The horizontal movement of the pedestal in relation to the base and the angular movement of the pointer in relation to the pedestal and base ensure that the micro-injector or other device can be properly positioned with regard to the organism which is the subject of the experiments.

The other important aspect of Applicants' invention is the use of magnetism to attach the pedestal to the base and the pointer to the pedestal. The use of magnetism provides even greater flexibility in the range of movement allowed, e.g., the pedestal may be turned from side-to-side on the base. Also, the magnetism dampens oscillation and other fine, unwanted movement and provides the stability required for very precise positioning.

For a more complete appreciation of the invention, attention is invited to the following detailed description of a preferred embodiment of the invention taken with the figure of the drawing. The scope of the invention, however, is limited only through the claims appended hereto.

DETAILED DESCRIPTION OF THE PREFERRED EMBODIMENT

Figure 1:
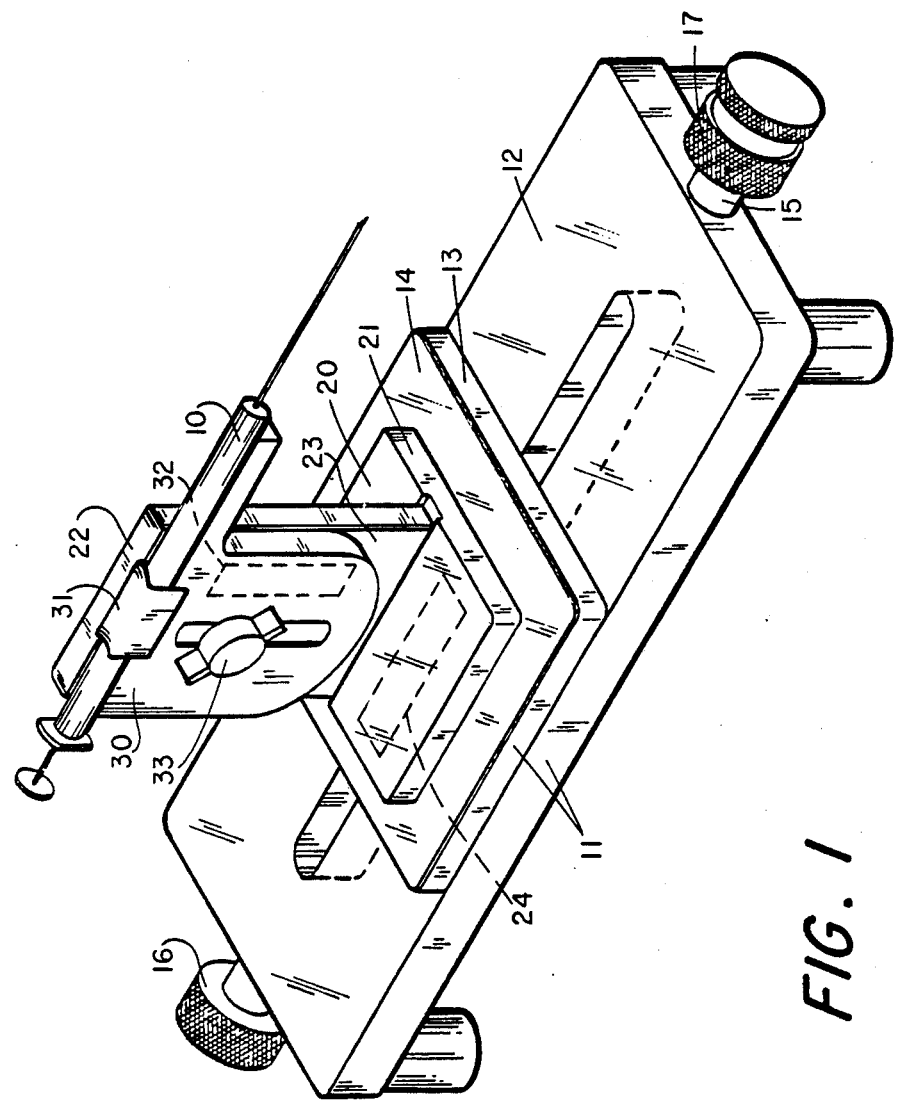
FIG. 1 illustrates one embodiment of the invention.

An illustrative embodiment of the invention is shown in FIG. 1 of the drawing, with the embodiment holding a micro-injector 10 which could be used to inject substances through the anal opening into the intestinal tract of a small organism such as a mosquito larva. The tip of the injector would be approximately 50 micron diameters with the larva anal opening not being much larger.

In this embodiment of the invention, a base 11 is comprised of a stand 12; a plate 13; and a metallic face plate 14. The metallic face plate 14 is composed of galvanized tin and is attached to the plate 13, on the side opposite to that which rests on the stand 12. The plate 13 moves slidably in a horizontal motion on, and in relation to, the stand 12.

A threaded rod 15, which is only partially shown, is attached to the stand 12 and is threadably engaged through a slot in the stand 12 with the plate 13. Adjustment knobs 16,17 are located at either end of the threaded rod 15 and can be used, either singley or together, to turn the rod 15. The threaded rod 15 permits horizontal movement of the plate 13 and metallic face plate 14 to be made in very small increments.

The pedestal 20 is comprised of a horizontal member 21 which is attached to the metallic face plate 14; a vertical member 22; and a second metallic face plate 23, composed of galvanized tin. As shown in FIG. 1, the vertical member 22 is placed in a slot in the horizontal member 21 and attached thereto. The second metallic face plate 23 is attached to the vertical member 22. Attached to the underside of the horizontal member 21 is a first magnetic strip 24.

The pedestal 20, in this embodiment, is attached to the metallic face plate 14 of the base 11 by means of magnetic force exerted on the metallic face plate 14 by the magnetic strip attached to the underside of the horizontal member 21.

The third major component of Applicants' invention is the pointer 30. The pointer 30 holds the micro-injector 10 or any other device to be used in conjunction with small organisms. The means of holding the device illustrated in FIG. 1 is a clip 31 but can be any comparable mechanism for securing the micro-injector 10 or similar device to the pointer 30.

The pointer 30 has a second magnetic strip 32 attached to its side. The magnetic strip holds the pointer 30 to the second metallic face plate 23 through magnetic force.

To further secure the pointer 30 to the pedestal 20, Applicants have provided for a threaded bolt (not shown) to be placed through a hole (not shown) in the vertical member 22 and second metallic face plate 23 of the pedestal 20 and then through a slot in the pointer 30 aligned with said hole. A nut 33 can be threaded onto the bolt to compress the pointer 30 and pedestal 20 together in fixed positions relative to each other. Applicants wish to emphasize that frequently the second magnetic strip 32 will be sufficient to hold the pointer 30 to the pedestal 20 without the need to tighten the nut 33.

In operation, the manipulator is placed next to the organism and then, through a combination of the motion permitted by the threaded rod and the magnetic strips 24,32, the device used to experiment on the organism under study is manipulated and positioned to effectuate the researcher's desired purposes. To enhance the effectiveness of the magnetic force in the magnetic strips 24,32, the stand 12, the plate 13, the horizontal member 21, the vertical member 22, and the pointer 30 may all be made of acrylic.

Applicants' invention provides for an apparatus with an extreme range of maneuverability. The ability to continuously, accurately, and variably adjust the height, angle, forward and backward movement of the manipulator provides the operator a far greater degree of freedom on the uses of the apparatus than is provided by anything in the prior art. Through the use of magnetized strips the ability to accurately vary positions is increased, while at the same time backlash, oscillation, settling and momentum are eliminated.

Increased flexibility and stability allow this manipulator to be used to position semi-micro pipettes, electrodes or other assemblages into very fine biological structures such as: nerves, sensory hairs, body cavities and other such structures. In this way, the researcher can apply test substances and small measurable forces and make physiological measurements.

We claim:

1. An apparatus for manipulating devices requiring precise positioning comprising:
    (a) a base, the base comprising a stand and a plate slidably attached for translational movement along the stand, wherein the plate is provided with a metallic face plate attached to the side of the plate opposite the side of the plate slidably attached to the stand;
    (b) means attached to the stand and the plate for controlling the translational movement of the plate in relation to the stand;
    (c) a pedestal slidably attached to the metallic face plate, the pedestal comprising a horizontal member which is slidably attached to the metallic face plate and a vertical plate member, wherein the horizontal member comprises at least one magnetic element attached to the side of the horizontal member in contact with the metallic face plate for allowing the slidable positioning of the pedestal on the metallic face plate, and wherein the vertical plate member is provided with a second metallic face plate attached to one side of the vertical plate member;
    (d) second plate means attached to the pedestal for adjustably supporting the devices requiring precise positioning, wherein the second plate means comprises at least one magnetic element attached to the side of the second plate means in contact with the second metallic face plate so that the second plate means is slidably attached to the second metallic face plate and so that the second plate means can be rotationally and translationally moved to another position on the second metallic face plate; and
    (e) means for controlling translational and rotational movement of said second plate means relative to the second metallic face plate.

2. The apparatus as recited in claim 1, wherein said movement control means comprises:
    (a) a threaded rod, said rod being fixedly connected to said stand and threadably engaged with said plate; and
    (b) a means for turning said rod to move said plate.

3. The apparatus as recited in claim 1, wherein said vertical plate member and said horizontal member are made of nonmagnetic material.

4. The apparatus as recited in claim 1, wherein the stand and the plate are made of nonmagnetic material.

5. The apparatus as recited in claim 4, wherein said nonmagnetic material is acrylic.

6. The apparatus as recited in claim 1, wherein vertical plate member and the plate means are made of nonmagnetic material.

7. The apparatus as recited in claim 1, wherein the means for controlling translational and rotational movement comprises:
    a threaded bolt, said bolt passing through aligned holes in said vertical plate member, said metallic face plate, and said plate means; and
    a nut, said nut being threadably engaged with said bolt so as to compress together in a fixed position said vertical plate member, said second metallic face plate and said plate means.

8. An apparatus for manipulating devices requiring precise positioning comprising:
    (a) a stand;
    (b) a threaded rod, said rod being fixedly connected to said stand;
    (c) a plate, said plate being slidably attached to said stand by being threadably engaged with said rod;
    (d) a means for turning said rod to move said plate;
    (e) a metallic face plate attached to said plate;
    (f) a horizontal member, said horizontal member being slidably attached to the metallic face plate;
    (g) a magnetic strip attached to said horizontal member, said strip being also magnetically attached to said metallic face plate so that the horizontal member can be repositioned and reattached to said metallic face plate;
    (h) a vertical member, said vertical member being attached to said horizontal member;
    (i) a second metallic face plate, said metallic face plate being attached to said vertical member;
    (j) a means for supporting said devices requiring precise positioning; and
    (k) a second magnetic strip attached to said devices supporting means, said strip being also magnetically attached to said second metallic face plate.

* * * * *